US012367985B2

(12) United States Patent
Cox et al.

(10) Patent No.: US 12,367,985 B2
(45) Date of Patent: Jul. 22, 2025

(54) DIGITAL TWIN OF A PERSON

(71) Applicant: KONINKLIJKE PHILIPS N.V., Eindhoven (NL)

(72) Inventors: Lieke Gertruda Elisabeth Cox, Eindhoven (NL); Valentina Lavezzo, Heeze (NL); Murtaza Bulut, Eindhoven (NL); Cornelis Petrus Hendriks, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 230 days.

(21) Appl. No.: 16/704,641

(22) Filed: Dec. 5, 2019

(65) Prior Publication Data
US 2020/0203020 A1    Jun. 25, 2020

Related U.S. Application Data

(60) Provisional application No. 62/781,755, filed on Dec. 19, 2018.

(51) Int. Cl.
*G16H 50/50* (2018.01)
*G16H 10/60* (2018.01)
(Continued)

(52) U.S. Cl.
CPC .............. *G16H 50/50* (2018.01); *G16H 10/60* (2018.01); *G16H 30/20* (2018.01); *G16H 50/70* (2018.01)

(58) Field of Classification Search
CPC ........ G16H 10/60; G16H 30/20; G16H 50/70; G16H 50/50
See application file for complete search history.

(56) References Cited

U.S. PATENT DOCUMENTS 8,918,162 B2 * 12/2014 Prokoski .............. A61B 5/0064
600/475
2007/0014452 A1 * 1/2007 Suresh ................. G06T 7/0012
382/128
(Continued)

OTHER PUBLICATIONS

Diaz, V., "Your doctor could soon be treating your virtual twin as a digital patient". Sep. 28, 2015. Wareable News. http://www.wareable.com/health-and-wellbeing/doctor-virtual-twin-digital-patient-ucl-887.
(Continued)

*Primary Examiner* — Fonya M Long
*Assistant Examiner* — Anthony Balaj

(57) ABSTRACT

A method of developing a personalized digital model of an anatomy of a person by a computer system comprising a processor arrangement and a communication module. The processor arrangement receives input data on an actual physical condition of the person from the communication module; searches a database of digital models modelling different physical conditions and selects a digital model from said database that closely matches the actual physical condition of the person based on some received input data; personalizes the selected digital model by developing the modelled physical condition of the selected digital model with a physiological development model based on received input data such that the developed modelled physical condition closely resembles said actual physical condition; and generates an output of the personalized digital model of said person on a data storage medium. Also disclosed, a computer program product and computer system for implementing the method.

20 Claims, 4 Drawing Sheets

(51) Int. Cl.
*G16H 30/20* (2018.01)
*G16H 50/70* (2018.01)

(56) References Cited

U.S. PATENT DOCUMENTS

| | | | | |
|---|---|---|---|---|
| 2011/0317890 | A1* | 12/2011 | Baroni | G06T 17/00 |
| | | | | 382/128 |
| 2013/0113798 | A1* | 5/2013 | Nahum | A61B 5/1176 |
| | | | | 345/420 |
| 2013/0317803 | A1* | 11/2013 | Manley | G06Q 10/067 |
| | | | | 703/21 |
| 2013/0325493 | A1* | 12/2013 | Wong | G16Z 99/00 |
| | | | | 705/2 |
| 2014/0279754 | A1* | 9/2014 | Barsoum | G06N 7/01 |
| | | | | 706/12 |
| 2015/0004584 | A1* | 1/2015 | Galibois | G09B 23/303 |
| | | | | 434/270 |
| 2016/0063726 | A1* | 3/2016 | Wenzel | G06T 7/12 |
| | | | | 382/128 |
| 2016/0070878 | A1* | 3/2016 | Soper | G16H 50/50 |
| | | | | 703/11 |
| 2016/0148372 | A1* | 5/2016 | Itu | G06F 18/217 |
| | | | | 382/128 |
| 2016/0210435 | A1 | 7/2016 | Comaniciu et al. | |
| 2017/0071484 | A1* | 3/2017 | Strachan | G16Z 99/00 |
| 2017/0177822 | A1* | 6/2017 | Fogel | G16H 50/20 |
| 2017/0235915 | A1* | 8/2017 | Mansi | G16H 50/30 |
| | | | | 705/3 |
| 2017/0286572 | A1 | 10/2017 | Dell'Anno et al. | |
| 2017/0293700 | A1* | 10/2017 | Bazaz | G06F 17/40 |

OTHER PUBLICATIONS

Mathematical modelling for the Digital Patient. Discipulus—288143, May 2013.
Soldiers digital twins let US Army 30 print replacement body parts in battle. http://www.fanaticalfuturist.com/2017/01/digital-clones-will-let-us-army-3d-print-new-bod-parts-in-battle-to-treat-injured-soldiers/.
Otake, Y. et al. "Supervised learning of anatomical structures using demographic and anthropometric information". John Hopkins University. Pattern Recognition Applications and Methods—International Conference, ICPRAM 2013, Revised Selected Papers, 2015, pp. 225-240.
Bruynseels, K. et al., "Digital Twins in Health Care: Ethical implications of an emerging engineering paradigm." Frontiers in Genetics, 9 [31]. http://doi.org/10.3389/fgene.2018.00031.
https://www.biodigital.com/.
http://www.vph-institute.org/.
Neal, M.L. et al., "Current progress in patient-specific modeling". Brief Bioinform. Jan. 2010; 11(1): 111-126.
Ceresa, M. et al., "Coupled immunological and Biomechanical Model of Emphysema Progression." 2018, Frontiers in Physiology, published Apr. 19, 2018, doi: 10:2289/fphys.2018.00388.
Weinans, H. et al., "The behavior of adaptive bone-remodeling simulation models." Journal of Biomechanics, vol. 25, No. 12, pp. 1425-1441, 1992.

* cited by examiner

DIGITAL TWIN OF A PERSON

FIELD OF THE INVENTION

The present invention relates to method of developing a personalized digital model of at least part of the anatomy of a (healthy) person with a computer system comprising a processor arrangement and a communication module under control of the processor arrangement.

The present invention further relates to a computer program product for implementing such a method on such a computer system.

The present invention further relates to a computer system product adapted to implement such a method.

BACKGROUND OF THE INVENTION

In many developed countries, the provision of healthcare is becoming increasingly strained. Some reasons for this include the growth of the population and increasing life expectancy. Unfortunately, although people live longer, the average age at which their health deteriorates to the point where regular medical care is required is not increasing accordingly, such that the ageing population is unwell for longer, which increases the pressure on the healthcare system, e.g. on medical practitioners, medical infrastructures such as hospitals, diagnostic equipment therein, and so on. Hence, rather than simply increasing medical resources, for which the financial resources may not be available, there exists a need to improve the efficiency of such healthcare systems.

A recent development in technology is the so-called digital twin concept. In this concept, a digital representation (the digital twin) of a physical system is provided and connected to its physical counterpart, for example through the Internet of things as explained in US 2017/286572 A1. Through this connection, the digital twin typically receives data pertaining to the state of the physical system, such as sensor readings or the like, based on which the digital twin can predict the actual or future status of the physical system, e.g. through simulation, as well as analyze or interpret a status history of the physical twin. In case of electromechanical systems, this for example may be used to predict the end-of-life of components of the system, thereby reducing the risk of component failure as timely replacement of the component may be arranged based on its end-of-life as estimated by the digital twin.

Such digital twin technology is also becoming of interest in the medical field, as it provides an approach to more efficient medical care provision. For example, the digital twin may be built using imaging data of the patient, e.g. a patient suffering from a diagnosed medical condition as captured in the imaging data, as for instance is explained by Dr Vanessa Diaz in https://www.wareable.com/health-and-wellbeing/doctor-virtual-twin-digital-patient-ucl-887 as retrieved from the Internet on 29 Oct. 2018. Such a digital twin may serve a number of purposes. Firstly, the digital twin rather than the patient may be subjected to a number of virtual tests, e.g. treatment plans, to determine which treatment plan is most likely to be successful to the patient. This therefore reduces the number of tests that physically need to be performed on the actual patient.

The digital twin of the patient for instance further may be used to predict the onset, treatment or development of such medical conditions of the patient using a patient-derived digital model, e.g. a digital model that has been derived from medical image data of the patient. In this manner, the medical status of a patient may be monitored without the routine involvement of a medical practitioner, e.g. thus avoiding periodic routine physical checks of the patient. Instead, only when the digital twin predicts a medical status of the patient indicative of the patient requiring medical attention based on the received sensor readings may the digital twin arrange for an appointment to see a medical practitioner to be made for the patient. This typically leads to an improvement in the medical care of the patient, as the onset of certain diseases or medical conditions may be predicted with the digital twin, such that the patient can be treated accordingly at an early stage, which not only is beneficial to the patient but can also reduce (treatment) costs. Moreover, major medical incidents that the patient may be about to suffer may be predicted by the digital twin based on the monitoring of the patient's sensor readings, thereby reducing the risk of such incidents actually occurring. Such prevention avoids the need for the provision of substantial aftercare following such a major medical incident, which also alleviates the pressure on a healthcare system otherwise providing such aftercare.

Such remote monitoring of a patient may lead to an infrequent need for the patient to physically meet a healthcare professional. However, a drawback of this approach is that such a digital model is only generated when someone has developed a medical condition to such an extent that clinically relevant data based on which a personalized digital model of the patient can be built has been collected, such as imaging data. Hence, there exists a need to monitor individuals with such digital twin technology at an earlier stage, such as a stage in which such imaging data is not yet available, for example because the individual has not yet developed any medical condition (i.e. is healthy) or such a medical condition is still in its early stages such that the clinical data required to build a personalized digital model of such an individual is not yet available, to further assist medical healthcare professionals as well as assist such persons in managing lifestyle or the like in order to reduce the onset of such diseases.

SUMMARY OF THE INVENTION

The present invention seeks to provide a computer-implemented method that can be used to develop a personalized digital model of at least part of the anatomy of a person regardless of the medical condition of that person.

The present invention further seeks to provide a computer program product for implementing such a method on a suitable computer system.

The present invention further seeks to provide a computer system adapted to implement such a method.

According to an aspect, there is provided a method of developing a personalized digital model of at least part of the anatomy of a person with a computer system comprising a processor arrangement and a communication module under control of the processor arrangement, the method comprising, with said processor arrangement, receiving input data relevant to an actual physical condition of at least part of the anatomy of the person with the communication module; searching a database of digital models modelling different physical conditions of said at least part of the anatomy; selecting a digital model from said database that most closely matches the actual physical condition of the at least part of the anatomy of the person based on at least some of the received input data; personalizing the selected digital model by developing the modelled physical condition of the selected digital model with a physiological development model associated with said selected digital model based on the received input data such that the developed modelled physical condition more closely resembles said actual physical condition in accordance with said input data; and generating an output of the personalized digital model of said person for storage on a data storage medium.

In this manner, the present invention provides a method to generate a digital model (also referred to as a digital twin in the remainder of this application) of an individual or person without the need for such a person to have developed a medical condition or disease to such an extent that such a personalized digital model would typically be constructed based on patient specific clinical data, e.g. medical imaging, acquired during investigations of the health concerns of the patient. Instead, the provision of a database in which a plurality of digital models that each represent the same anatomy (or part thereof) of a human being in different physical conditions allows for a 'best guess' choice of one of these models as a starting point of a digital model of such a person based on input data provided to the method that is relevant to the physical condition of that person's part of the anatomy of interest, such as for example age, gender, weight, height, lifestyle parameters such as diet, activity levels, alcohol consumption, smoking habits and so on, medically relevant data pertaining to blood relatives of the person, genotype data, sensor data, as well as any available clinical data such as imaging data, clinical test results etcetera. Such user data (and any additional relevant data where available) may be used to personalize the digital model selected from the database, e.g. using a suitable algorithm, in order to provide the first digital model or digital twin of the person. Such data used for personalization may include a wide variety of types of data, such as the aforementioned user data as well as prenatal ultrasound images of the person, genotype and phenotype data, sensor device data from wearable sensors or mobile communication devices including sensors and so on. It is noted for the avoidance of doubt that all available data pertaining to such a person may be used for selection and/or personalization of such digital models, that is all data used for the selection of the digital model may also be used for its personalization, whereas alternatively at least some of the data may be dedicated data for the personalization of a selected digital model, and/or at least some of the data may be dedicated data for the selection of a digital model.

The physiological development model may represent a disease model of said at least part of the anatomy that can be used to predict the onset and progression of a particular disease affecting the (part of the) anatomy of interest, which prediction may be verified from time to time by further data pertaining to the actual physical condition of the person at that time being fed into the personalized digital model.

To this end, the method may further comprise predicting a development of the actual physical condition of the at least part of the anatomy of the person over time by developing the modelled physical condition of the personalized digital model with the physiological development model; and generating an output pertaining to said predicted development of the actual physical condition of said person. Such an output may be used to help the person avoid unwanted changes to his or her physical condition, e.g. avoid the onset of certain medical conditions, by making lifestyle changes for example. Alternatively, such an output may be directed at a healthcare professional for monitoring purposes and clinical decision support.

In example embodiments, the at least part of the anatomy of the person comprises one of an organ, a system of organs, a lumen system and a musculoskeletal system of the person.

The input data may comprise at least one of information belonging to the person and information belonging to a relative of the person. Importantly, due to genetic relationships between the person and his or her blood relatives, the information of such relatives, e.g. medical imaging data, digital models of such relatives and so on, may be used to improve the personalization of the digital model of the person.

In an embodiment, the method further comprises receiving further input data relating to an updated actual physical condition of the at least part of the anatomy of the person with the communication module; and updating the personalized digital model by developing the modelled physical condition of the personalized digital model with the physiological development model based on the received further input data. As previously mentioned, such further input data, which typically is received at a later point in time than the input data, may be used to validate the personalized digital model of the person of interest, e.g. by adjusting the geometry of the digital representation of the part of the anatomy of interest of the person and/or adjusting its simulated physical condition, e.g. by adjusting the actual position on a timeline of a disease progression model implemented by the physiological development model associated with the personalized digital model. In this manner, the personalized digital model, the physiological development model and/or a disease progression model may be updated, e.g. by updating parameters and characteristics of such models.

The method may further comprise generating an output comprising an indication of the updated modelled physical condition and transmitting said output to an electronic device registered to said person or a medical practitioner caring for said person as previously explained.

The method may further comprise adjusting the physiological development model based on the received further input data. For example, where the physiological development model simulates a disease progression, the rate of progression may be dependent on a number of parameters such as lifestyle parameters and physiological parameters. Hence, where the further input data indicates that some of these parameters have changed compared to the (initial) user data, the physiological development model associated with the personalized digital model may be updated accordingly.

Such changes in the input data of the model, e.g. changes in the lifestyle of physiology of the person of interest, may further warrant a verification of the digital model selected from the database of digital models. To this end, the method may further comprise comparing the further input data to the input data, and if said further data is significantly different to the input data, searching the database of digital models modelling different physical conditions of said at least part of the anatomy; selecting a further digital model from said database that most closely matches the actual physical condition of the at least part of the anatomy of the person based on at least some of the received further input data; personalizing the selected further digital model by developing the modelled physical condition of the selected further digital model with the physiological development model based on the received further input data such that the developed modelled physical condition more closely resembles said actual physical condition as described by said further input data; and generating an output of the personalized further digital model of said person for storage on the data storage medium. This for instance reduces the risk that a non-optimal digital model is used for the patient, which can lead to a local optimization problem in the data generated with the model.

The step of comparing the further input data to the input data may comprise predicting the further input data with the personalized digital model, and wherein the further input data is considered to be significantly different to the input data if said further input data cannot be accurately predicted with the personalized digital model. This provides a clear indication that the originally selected and subsequently personalized digital model is non-optimal, as validation of the predictive capabilities of this model using the further input data is not possible to a satisfactory degree in this scenario.

The selection of a further digital model from the database of digital models and subsequent personalization of this further digital model leads to a situation in which the person is associated with at least two personalized digital models. Of course, upon receiving yet further input data relevant to the actual physical condition of the relevant part of the anatomy of the person at later points in time, the method may produce additional personalized digital models as explained above. In such a situation, the method must decide which of the personalized models to use to accurately predict physiological changes to this part of the anatomy. To this end, the method may further comprise receiving second further input data indicative of a potential further change to the actual physical condition of at least part of the anatomy of the person with the communication module; predicting the second further input data with the personalized digital model and the personalized further digital model respectively based on a period of time elapsed between receiving the further input data and receiving the second further input data using the physiological simulation model; and selecting one of the personalized digital model and the personalized digital model as a working digital model based on the accuracy of the predicted second further input data with said models. The use of multiple personalized digital models to predict physiological changes to the anatomy of the person has the advantage that the risk of the occurrence of local maximization problems is further reduced.

As a further refinement, the method may further comprise deleting the personalized digital model or the personalized further digital model if the predicted second further input data generated with said model significantly deviates from the actual second further input data. Such a significant deviation for example may comprise a difference between the predicted second further input data generated with said model and the actual second further input data such that the predicted second further input data no longer can be considered statistically relevant.

According to another aspect, there is provided a computer program product for a computer system comprising a processor arrangement and a communication module under control of said processor arrangement, the computer program product comprising a computer readable storage medium having computer readable program instructions embodied therewith for, when executed on the processor arrangement, cause the processor arrangement to implement the method of any of the herein described embodiments. Such a computer program product for instance may be used to configure existing computer systems to implement the method according to embodiments of the present invention.

According to yet another aspect, there is provided a computer system comprising a processor arrangement and a communication module under control of said processor arrangement, wherein the processor arrangement is adapted to implement the method of any of the herein described embodiments. For example, the processor arrangement may be hard-coded to implement such a method or alternatively the computer system may further comprise the computer program product according to any of the herein embodiments of the present invention. Such a computer system may be used to generate and develop a digital model of a (healthy) person without the need for such a person to have entered the healthcare system as explained in more detail above.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
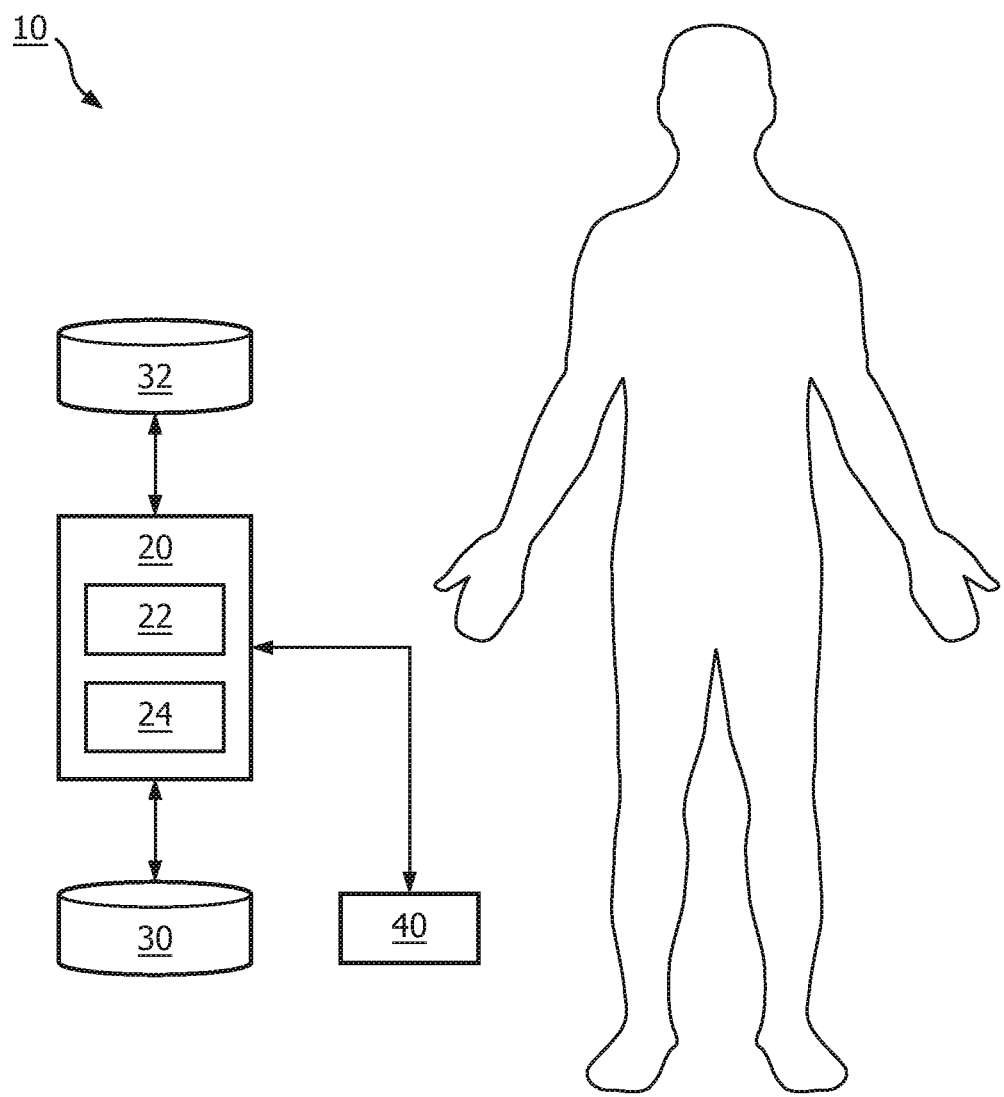
FIG. 1 schematically depicts a system for creating and developing a digital model of a person according to an embodiment.

It should be understood that the Figures are merely schematic and are not drawn to scale. It should also be understood that the same reference numerals are used throughout the Figures to indicate the same or similar parts.

FIG. 1 schematically depicts a generalised setup to which embodiments of the present invention are applicable. A physical condition, e.g. a health condition, of a person 10 is to be monitored by a digital model of at least a part of the anatomy of the person 10. Such a digital model, or digital twin, of the person 10 typically comprises an anatomical model, which may accurately reflect the anatomy of the person 10 if it is based on image data of the person's anatomy, and a parameterized physiological development model acting upon the anatomical model that predicts changes to a physiological state of the modelled anatomy, such as the onset or progression of a disease of the anatomy. The digital model for example may be a model of an organ or system of organs of the person 10, a lumen system such as the cardiovascular system, renal system or the pulmonary system of the person 10, a musculoskeletal system of the person 10, a brain model of the person 10, a blood chemistry model such as a blood glucose model of the person 10, and so on. The parameterized physiological development model may include an algorithm or set of algorithms creating the artificial intelligence of the digital model, which based on values of parameters pertaining to the person 10 can predict the physiological changes in the part of the anatomy of interest of the person 10 using the digital model, such as a rate of such physiological changes.

The parameters pertaining to the person 10 may include physiological parameters, e.g. heart rate, blood pressure, fractional flow reserve, respiration rate, blood chemistry parameters such as oxygen saturation level, blood glucose level, and so on. The parameters pertaining to the person 10 may further include lifestyle parameters, e.g. activity levels and type, smoking and drinking habits, and so on. Such parameters may be manually fed into the digital model using a user interface, may be automatically fed into the digital model, e.g. by an electronic device such as a sensor, smart phone, smart watch or the like, which monitors one or more parameters pertaining to the person 10, and so on. Further examples of such sensor data include (wearable) ultrasound sensor data, photo or laser scan data, e.g. of the brain, spirometry data, e.g. to obtain lung volume, skin fold measurement to obtain skin thickness, biomedical impedance analysis to determined body composition and so on. By feeding the digital model of the person 10 with such up to date parameters pertaining to the person 10, the predictions made with the digital model can be validated, and the digital model can be updated, e.g. in order to reflect changes to previously received parameter values, which changes for example may affect the rate of change to the anatomy modelled by the digital model, such as a change in the rate at which a physical condition such as a disease develops.

The physiological changes to the person's anatomy as predicted by his or her digital twin may be fed to the person 10 or a healthcare professional caring for the person 10, e.g. in the form of an electronic message to a user interface registered to that individual. In case of such information being directed at the person 10, he or she may use this information to make lifestyle changes, e.g. to slow down or avoid the onset of certain medical conditions or to seek medical care for example. Where such information is directed at a healthcare professional, he or she for example may use such information in clinical decision making processes, such as to develop a care plan for the person 10, schedule an appointment with the person 10 and so on.

As explained above, the digital model of the person 10 may be generated after the person 10 has sought medical attention, which may have led to the generation of imaging data of the (part of the) anatomy of interest of the person 10, e.g. MRI images, CT images, ultrasound images and so on. Such imaging data may be used to generate the anatomical part of the digital model of the person 10, thus yielding a highly accurate personalized digital model of the person's anatomy. However, where such (actual) imaging data is unavailable, the generation of a meaningful personalized digital model of the (part of the) anatomy of interest of the person 10 is far from trivial. Nevertheless, it is desirable to generate such a personalized digital model, as it facilitates the prediction of changes to a physical condition, e.g. the onset of a medical condition for the person 10 prior to the person having contacted a healthcare professional. This for example is beneficial in terms of prevention and more effective treatment or management of such medical conditions, which can lead to significant efficiency improvements in medical care.

In accordance with embodiments of the present invention, a database 30 of digital models of the (part of the) anatomy of interest of the person 10 is provided. Such models may be the digital models of different individuals, which may have been generated from imaging data or the like. The different digital models typically cover a wide variety of individuals in terms of gender, age, weight, lifestyle habits and so on. A computer system 20 comprising a processor arrangement 22 and a data communication module 24 is communicatively coupled to the database 30 over a data link. The processor arrangement 22 of the computer system 20 may take any suitable shape. In the context of the present invention, a processor arrangement may comprise one or more processors, processor cores and the like that cooperate to form such a processor arrangement. Similarly, the data communication module 24 may take any suitable shape, such as a wireless or wired data communication module, as is well known in the art and will therefore not be further explained for the sake of brevity only.

The data link may take any suitable shape, such as a wireless communication link, a wired communication link or a combination thereof. Any suitable communication protocol may be deployed between the one or more sensors and the communication module 24 over the data link 17. For example, in case of a wireless communication link, the communication protocol may be Wi-Fi, Bluetooth, a mobile phone communication protocol such as 3G, 4G, 5G and so on. Other examples of suitable wireless communication links will be immediately apparent to the skilled person. In case of a wired communication link, suitable application protocols may include TCP/IP and similar protocols used to communicate over a wired data communication link such as a wired network, e.g. the Internet.

The computer system 20 is further coupled to a user interface 40 through which the user, e.g. the person 10 or a healthcare professional responsible for the medical care of the person 10 provides data pertaining to the person 10 as input data to the computer system 20. Such a user interface may take any suitable shape, e.g. a computer terminal, a peripheral device to the computer system 20, a mobile communication device such as a smart phone or tablet computer and so on.

Figure 2:
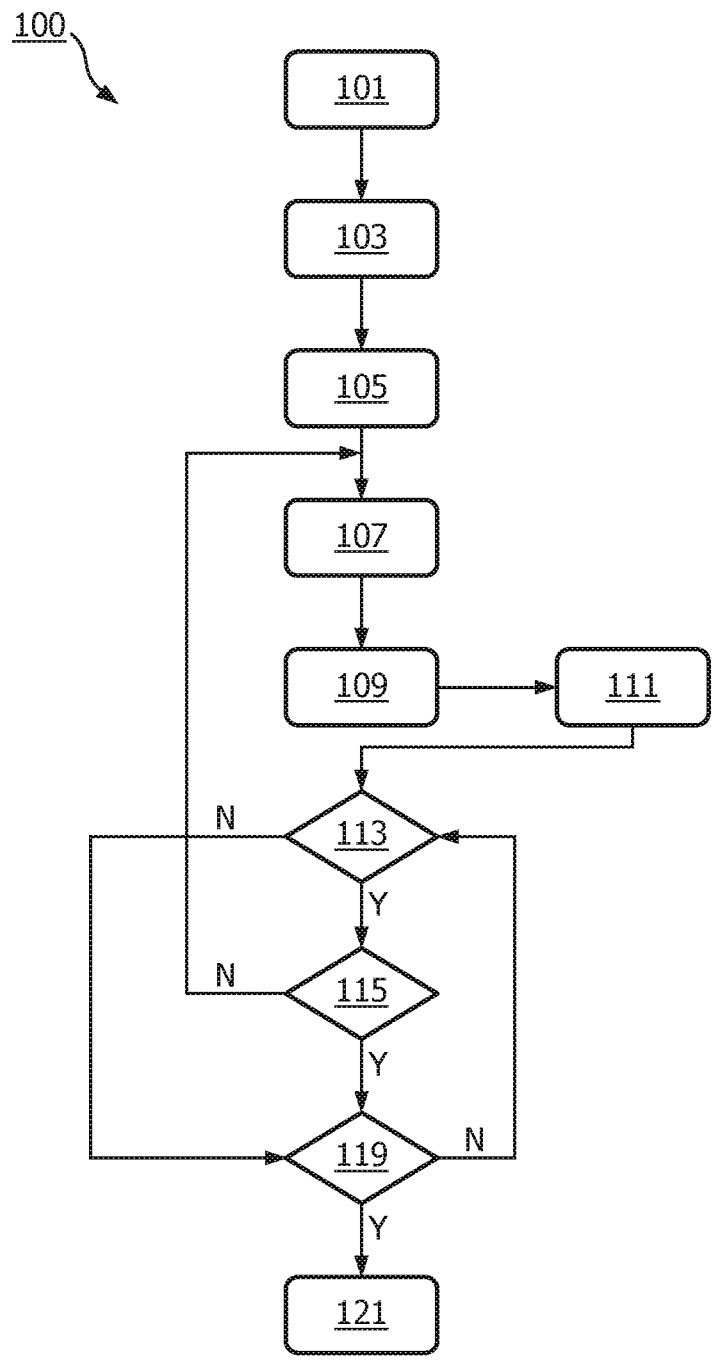
FIG. 2 depicts a flowchart of a method for creating and developing a digital model of a person according to an embodiment.

The computer system 20 is tasked with generating a digital model of the (part of the) anatomy of interest of the person 10. To this end, the processor arrangement 22 is arranged to implement the method 100, a flowchart of which is shown in FIG. 2. The method 100 starts in operation 101, e.g. by starting up the computer system 20, after which the method 100 proceeds to operation 103 in which the processor arrangement 22 receives the user information pertaining to the person 10 from the user interface 40, e.g. through the data communication module 24. This input data is used by the processor arrangement to select the digital model from the database 30 that best matches the anatomy of the person 10. The input data may comprise information such as the gender, age, weight, lifestyle information, imaging data, physiological measurements (such as EEG, ECG, EMG, blood pressure, skin conductance, etc.), lab test data and so on, as previously explained.

In operation 105, the processor arrangement 22 accesses the database 30, e.g. through the data communication module 24, and searches the database to find a digital model that best matches the input data received in operation 103. For this purpose, the processor arrangement 22 may deploy a matching algorithm as will be readily understood by the skilled person.

Next, the processor arrangement 22 personalizes the selected digital model in operation 107 such that this model more closely resembles the anatomy and its physiological condition of the person 10. This may be achieved using the input data received in operation 103 as well as by using additional input data pertaining to the person 10, which additional input data may be received by the processor arrangement 22 at any suitable point in time, e.g. in operation 103 or any other point in time, e.g. using a suitable algorithm. Such personalization for example may include adjusting the anatomical model and/or updating parameters in the parameterized physiological development model based on the provided input data pertaining to the person 10. Such an algorithm for example may utilize (statistically) known relationships between the data pertaining to the person 10, e.g. the person's age, weight, gender, etcetera and dimensions of the anatomy, or may be trained using artificial intelligence on the available datasets, for example using principal component analysis. The additional input data may comprise any selection of a wide variety of types of data from which the anatomy of the person 10 and its physical state can be estimated. This may be data belonging to (i.e. derived from) the person 10 him or herself or data belonging to (i.e. derived from) a blood relative of the person 10. The data belonging to the blood relative may provide a good estimate of the data belonging to the person 10 due to the genetic relationship between the person 10 and his or her blood relative. Upon personalizing the selected digital model, the processor arrangement may store the personalized digital model on a data storage medium 32, which may form part of the database 30 or form part of the computer system 20, e.g. a hard disk, solid state storage device, memory and so on, or alternatively may be a separate entity, e.g. networked storage device, a cloud storage arrangement and so on.

The personalized digital model may be used by the processor arrangement 22 to predict (physiological) changes to the corresponding anatomy of the person 10 in operation 109 as explained in more detail above. Such predicted changes may include the predicted onset or development of a medical condition such as a disease affecting the corresponding anatomy of the person 10. This for example may be achieved using the parameterized physiological development model of the personalized digital model, in which the personalized parameters in this model may predict a rate of physiological change of the modelled anatomy of the person 10, e.g. by predicting a physiological condition of the modelled anatomy after a defined period of time has elapsed. As will be understood by the skilled person, such a rate of change is typically a function of the parameters used by the parameterized physiological development model of the personalized digital model, such that this rate may change upon the values of such parameters changing.

The predicted physiological changes to the modelled anatomy of the person 10 may be included in an output generated with the processor arrangement in operation 111. Such an output for example may take the form of an electronic message for the person 10 or a healthcare professional tasked with caring for the person 10. The electronic message may be visualized on a user interface such as the user interface 40 or another user interface, e.g. the display of a computer or mobile communication device in the possession of the person 10 or the healthcare professional, for the purpose of informing the person 10 or healthcare professional accordingly, as explained in more detail above.

In an embodiment of the method 100, the processor arrangement 22 may check in operation 113 if further input data pertaining to the physical condition of the modelled anatomy of the person 10 has been received. If this is not the case, the method 100 may proceed to operation 119 in which it is decided if the method 100 is to be terminated. If this is the case, the method 100 ends in operation 121. Otherwise, the method 100 reverts back to operation 113 in which the processor arrangement 22 waits for updated input data to be provided through the user interface 40 for instance. Of course, in the meantime the processor arrangement 22 may continue to (periodically) predict the physiological development of the modelled anatomy of the person 10 and produce an output comprising this prediction as explained above.

Once the processor arrangement 22 receives such further input data in operation 113, the processor arrangement 22 proceeds to operation 115 in which the received further input data is used to validate the personalized digital model. Such validation for example may include comparing the received further input data with expectation values of the further input data produced by the digital model at the point in time at which the further input data has been acquired. In case the received further input data and expectation values of the further input data are sufficiently comparable, e.g. do not differ from each other by more than a defined amount, or have the same value, there is no need to update the (parameters of the) digital model, such that the method 100 may proceed to previously described operation 119. On the other hand, if it is determined in operation 115 that the digital model is unable to accurately predict the expectation values of the further input data, or the further input data indicates that certain values in the digital model that are treated as constants, such as lifestyle parameters, have changed, the method 100 may revert back to operation 107 in which the processor arrangement 22 updates the personalized digital model based on the received further input data such that the personalized digital model more closely resembles the actual physiology of the modelled anatomy of the person 10.

Figure 3:
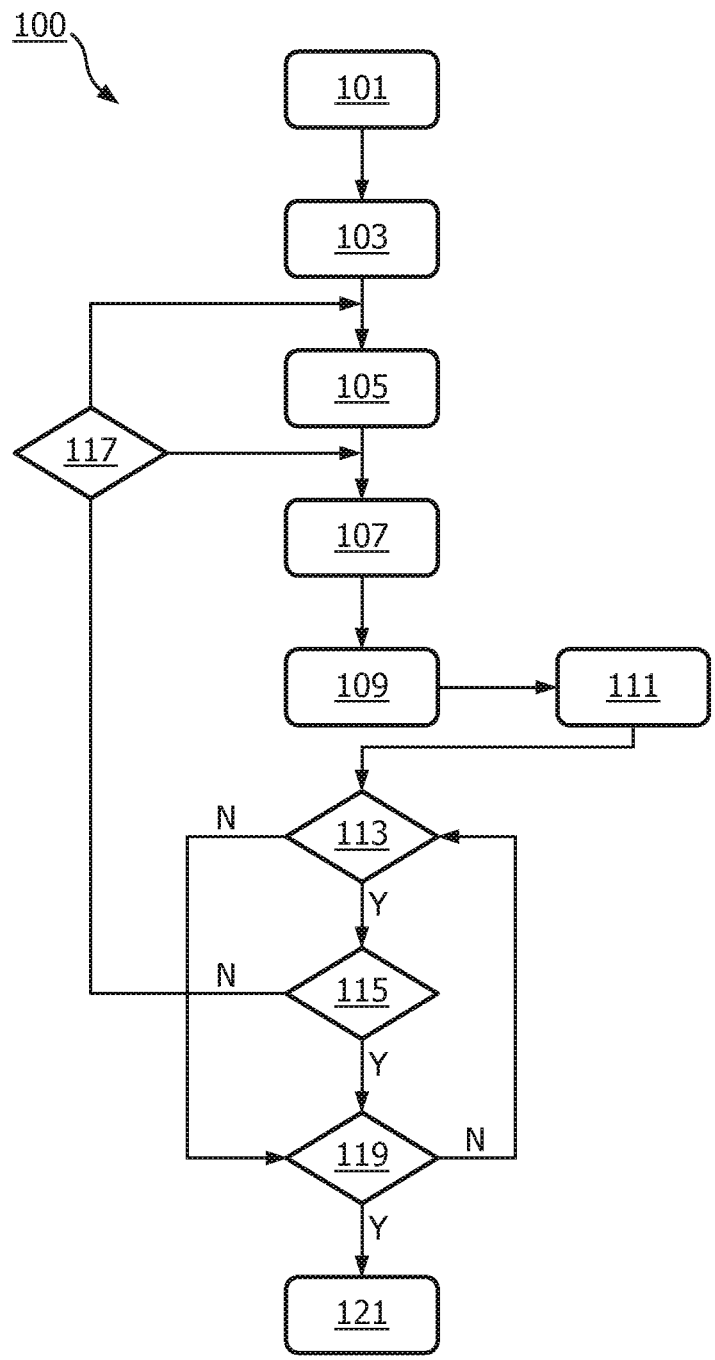
FIG. 3 depicts a flowchart of a method for creating and developing a digital model of a person according to another embodiment.

A further refinement to the validation operation 115 in the method 100 is depicted by the flowchart of FIG. 3. This embodiment is based on the realization that the personalized digital model of the person 10 may be or have become non-optimal, e.g. due to changes to the input data pertaining to the person 10 over time. Such a non-optimal digital model may give rise to local maximization problems for example. In accordance with this embodiment, following the received further user data in operation 113 and the failed validation of the personalized digital model in operation 115, the method 100 may proceed to operation 117 in which the processor arrangement 22 may compare the properties of the further user data as received in operation 113 with the properties of the originally received user data in operation 103. This comparison for example may be done by calculation of similarity between two sets of data by applying statistical methods or based on predictive machine learning techniques such as convolutional neural networks. For example, the processor arrangement 22 may check if the distribution of the further input data and the original input data are statistically significantly different from each other, or if the values from the further input data can be predicted using the data models developed from the original input data, respectively. If such differences are significant or above a calculated or defined threshold, respectively, the method 100 reverts back to operation 105 in which the processor arrangement selects a new digital model from the database 30 and personalized using the further input data in operation 107 as previously explained.

At this point there are two personalized digital models associated with the person 10, such that the processor arrangement 22 needs to decide which of the associated digital models to select as a representative or working model for the person 10. Such a model selection may be based on simulation results with the respective models. For example, the respective personalized digital models may be used to simulate updated input data pertaining to the person 10 to be received at a future point in time, such that upon receipt of this data at that point in time the model whose simulated data most closely resembles the actually received updated input data may be selected as the working model. It should be understood that this embodiment of the method 100 is not limited to the association of a pair of personalized digital models to the person 10. The selection of additional digital models for the person 10 may be repeated every time the computer system 20 receives updated input data pertaining to the person 10, e.g. from the user interface 40.

Hence, in this manner the computer system 20 may operate multiple representative models for the person 10. As long as each of these digital models are able to predict future input data pertaining to the person 10 to a satisfactory degree, such personalized digital models may be retained, as at some point in time they may become the working model again, given that it typically is not known or predictable how the health of the person 10 will develop and change.

When such new input data pertaining to the person 10 becomes available, each of the personalized digital models associated with the person 10 may be validated in operation 115. Only where such a personalized digital model is no longer capable to reproduce the received input data to a satisfactory degree, e.g. because the variance between the predicted values of the input data and the actually received input data values is so large that the predicted values have become statistically irrelevant, may the personalized digital model be deleted.

The present invention will now be illustrated in more detail by the following examples. It should be understood that these examples are not intended to limit the scope of protection conveyed by the claims of the present application.

Example 1: Personalized Digital Model on the Organ of a Person 10

In this example, the database 30 contains medical images of the organ to model, from which the processor arrangement 22 selects the medical image that is the best match with the person 10, based on data available for the person 10 and the organ in the database, e.g. age, gender, weight, and so on, as explained in more detail above. This may be achieved using artificial intelligence (AI), e.g. by first training an algorithm on an available database of images to find the best match for a new organ using available parameters. For example, for each image in the database the best match is determined using similarity search techniques as ground truth, after which the algorithm is trained to select the parameters that best predict the correct match.

Once the digital organ model has been selected, the selected model is personalized. Such personalization is desirable since it is likely that not all parameters of the person 10 are an exact match with those of the selected model, such that the selected digital model can be updated to better match the organ of the user. This can either be done via (statistically) known relationships, e.g. between a person's weight, height, age, etc. and organ dimensions, properties, and so on, or via another AI algorithm trained on the available datasets, e.g. using principal component analysis.

Potentially, a wide variety of data could be taken into account to personalize the selected digital organ model, including, prenatal ultrasound images, which may be used to derive organ shape as well as initial size and, in case of multiple images, growth rate; (medical) images (e.g. CT, MRI, ultrasound) from relatives such as parents, siblings; parameters of the person 10 that are related to the organ size and growth rate, e.g. gender, age, height, weight, and so on, which therefore may be used to predict current and future physical conditions of the organ from a previously determined physical condition; laboratory test values of e.g. hormones that influence growth rates such as oestrogen, testosterone, insulin and, leptin to predict current and future physical conditions of the organ from a previously determined physical condition; genotype and phenotype data; lifestyle information pertaining to the person 10 such as information regarding nutrition, smoking, alcohol consumption, medication and physical exercise habits where relevant, symptoms experienced by the person 10 and questionnaires regarding the person 10; wearable and/or mobile communication device data, such as data pertaining to physiological parameters such as activity, heart rate, respiration rate, and so on; additional sensor data, which may include but is not limited to wearable ultrasound sensor data, photo or laser scan data, spirometry data, fold measurement data, and biomedical impedance analysis data; and digital organ models of relatives to derive features that are known to have a significant genetic component, such as risk factors for disease development, growth curves, and so on.

Once the first personalized digital model of the organ of the person 10 has been created, it continually may be updated when new input data pertaining to the organ of the person 10 becomes available, as explained more generally above.

Example 2: Digital Model of a System of Organs

As in example 1, in this example a digital model of an organ of the person 10 is selected, built and modified as previously explained. However, sometimes the clinician is not only interested in how a specific organ is functioning, but also in how the organ is interacting with the entire system in which it is embedded or how the organ is interacting with other organs. Indeed, some organs may be directly linked to their systemic counterpart such as the relationship of the heart with the full cardiovascular system, but sometimes such relationships are more hidden, such as for example the relationship between the mouth and kidneys in the modelling of diabetes. Depending on the physical condition of the person 10, such relationships may also become important.

In this example, the selection process of the digital model in operation 105 not only includes the selection of the most appropriate organ model for the person 10, but also its relationship with organs in the system and/or surrounding or related organs. These relationships may be included in the form of a systemic model such as a Bayesian model or a biophysical model similar to that of the digital organ model. Machine learning algorithms again may be used to support the selection process and identify the relationships to build the digital model of the full organ system of the person 10. Alternatively, a digital model representing such a system of organs may be built by combining organ models acquired in different ways. For example, for a specific organ a personalized digital model may exist based on previously acquired imaging data, whilst for another organ the digital model is personalized by selecting the model from a database of models and subsequent personalization of the selected model as explained in detail within the present application, after which both models may be combined to define a model of the system of organs.

Example 3: Transition from a Healthy Digital Twin Organ to a Diseased Digital Twin Organ: Predict the Onset and Progression of a Disease A specific application example for the teachings of the present invention is the onset and progression of lung emphysema due to smoking. Inflammation reactions due to the inhalation of solid particles (smoking) slowly alter the mechanical properties of the healthy lung tissue, which in turn alter the local mechanical forces which act on the lung tissue during respiration. At some point in time the local stress becomes too high, and alveolar walls start to rupture, which is commonly referred to as emphysema. This again alters the stress field but at a much higher rate. This progressive molecular-biomechanical process is accessible for numerical modelling using a digital model of the pulmonary system of the person 10.

The input parameters of such a digital model may include one or more indicators of the exposure of the person 10 to harmful stimuli, such as a smoking indicator specifying the smoking habits such as the frequency and intensity of smoking by the person 10, an air pollution indicator specifying air quality at a location associated with the person 10, and so on. Such one or more input parameters allow the simulation and prediction of how (quickly) this exposure will transform a healthy lung of the person 10 into a diseased lung. For instance, in case of a smoking indicator, it is possible to simulate and predict how this transformation process may be influenced or halted by changes to the person's smoking behaviour, e.g. by altering the smoking indicator is a systematic manner.

The relevance of this example is twofold. Firstly, it illustrates that it is important to already utilize a digital model when the organ of the person 10 is still healthy. Secondly, it illustrates how a digital twin of a healthy organ "can become ill" due to harmful factors, without having to define a new digital twin after the onset of a disease.

Figure 4:
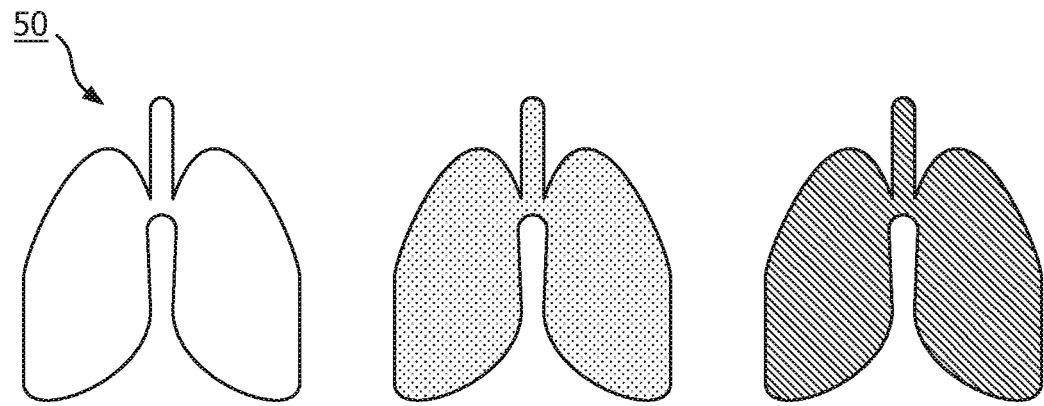
FIG. 4 schematically depicts a disease progression model implemented by a digital model of a person according to an example embodiment.
Figure 4:
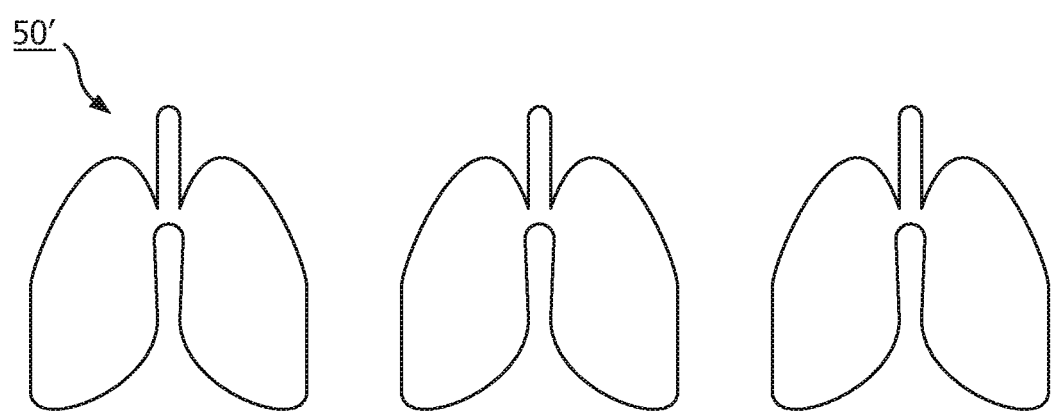

Based on this digital model it is for example possible to simulate images and/or generate metrics that indicate the current and future state of the lung, taking into account the current and future smoking behaviour. This is schematically depicted in FIG. 4, which depicts simulated images of a physical condition of a lung at age 20 (left image), age 40 (middle image) and age 60 (right image) for a person 10 continuing to smoke (images 50) and giving up smoking (images 50'). Such information can be communicated to end users in different ways, depending on the target group and goal. For example, a young adult might be sensitive to future fitness levels or financial consequences while an adult in mid-life might be sensitive to predicted remaining healthy life. In contrast, a physician might be more interested in the metrics themselves in order to select optimal treatment plans.

Example 4: Digital Twin of Musculoskeletal System

In this example, the matching digital model that is selected from the database 30 and subsequently personalized based on the available input data is for creating one or more digital twins of the musculoskeletal system. Such digital twin(s) for example may be used to predict (the risk of) osteoporosis development. Although part of this development risk is genetically determined, controllable factors (parameters) such as activity, alimentation, medication and hormones play an important role in such development.

It is known per se simulations of bone remodeling have been performed, but such simulations generally require a starting geometry and/or bone mineral density for the digital model of the musculoskeletal system. Such data can be acquired using CT scans, but as such exposure to radiation increases the risk of developing cancer, the American College of Radiology advises that such imaging exams are only performed if there is a clear medical need.

As such, it may be beneficial to perform the simulations based on a best matched digital model from a database to predict the future development of bone density of the person 10, taking into account personal parameters such as activity, alimentation, medication, and so on. Such modeled data may be used to guide the person 10 or his or her healthcare practitioner in making lifestyle changes to prevent (further) development of osteoporosis.

The above described embodiments of the method 100 executed by the processor arrangement 22 may be realized by computer readable program instructions embodied on a computer readable storage medium having, when executed on a processor arrangement 22 of a computer system 20, cause the processor arrangement 22 to implement any embodiment of the method 100. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the computer system 20 is adapted to retrieve the computer readable program instructions from such a computer readable storage medium and to create a new computer readable storage medium by storing the retrieved computer readable program instructions in a data storage arrangement 30 accessible to the computer system 20, e.g. in a memory device or the like forming part of the computer system 20.

The computer system 20 may be adapted to implement the embodiments of the method 100 by hard-coding the various steps and operations of the method 100 into the processor arrangement, e.g. by the provision of one or more ASICs .designed for this purpose. Alternatively, the computer system 20 may comprise the aforementioned computer program product communicatively coupled to the processor arrangement 22 such that the processor arrangement 22 may include one or more general purpose processors capable of executing the computer readable program instructions embodied thereon.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method of developing a personalized digital model of an organ or system of organs of a person with a computer system comprising a processor arrangement and a communication module under control of the processor arrangement, the method comprising, with said processor arrangement:

receiving input data relevant to an actual physical condition of the organ or system of organs of the person via the communication module over a first period of time, at least a portion of the input data being received from a wearable sensor device;

searching an anatomical model database of digital models modelling different physical conditions of said organ or system of organs and automatically selecting a digital model from said anatomical model database, wherein the selected digital model comprises an anatomical model for modelling the organ or system of organs and a physiological development model configured to predict changes to a physical condition of the modelled organ or system of organs, wherein the anatomical model of the digital model that is automatically selected most closely matches the actual physical condition of the organ or system of organs of the person based on at least some of the input data;

personalizing the selected digital model by developing a modelled physical condition of the selected anatomical model with the physiological development model based on the input data and adjusting the anatomical model such that the modelled physical condition more closely resembles said actual physical condition in accordance with the input data;

predicting, using the physiological development model, a change to the physical condition of the modelled organ or system of organs;

receiving further input data relevant to the actual physical condition of the organ or system of organs over a second time period later than the first time period;

verifying the prediction made by the physiological development model based, at least partially, on a comparison between the predicted change to the physical condition of the modelled organ or system of organs and the further input data; and when the predicted change to the physical condition of the modelled organ or system of organs differs from the further input data by at least a defined threshold:
  searching the anatomical model database and automatically selecting a further digital model from the anatomical model database, wherein the selected further digital model comprises an further anatomical model for modelling the organ or system of organs and a further physiological development model configured to predict changes to a physical condition of the modelled organ or system of organs, wherein the further anatomical model of the digital model that is automatically selected most closely matches the actual physical condition of the organ or system of organs of the person based on at least some of the further input data; and
  personalizing the selected further digital model by developing a further modelled physical condition of the further anatomical model with the further physiological development model based on the further input data and adjusting the further anatomical model such that the further modelled physical condition more closely resembles said actual physical condition in accordance with the further input data;

wherein the further digital model that is automatically selected is different from the digital model that was previously automatically selected.

2. The method of claim 1, further comprising:
predicting an onset, treatment, or development of the actual physical condition of the organ or system of organs of the person over time by developing the modelled physical condition of the personalized digital model with the physiological development model; and
generating an output pertaining to said predicted development of the actual physical condition of said person.

3. The method of claim 1, wherein the physiological development model represents a disease model of said organ or system of organs.

4. The method of claim 1, wherein the input data further comprises at least one of information belonging to the person and information belonging to a relative of the person, wherein the at least one of information comprises at least one of a gender, age, weight, imaging data, and lab test data.

5. The method of claim 1, further comprising:
receiving the further input data relating to an updated actual physical condition of the organ or system of organs of the person with the communication module; and
updating the personalized digital model by developing the modelled physical condition of the personalized digital model with the physiological development model based on the received further input data.

6. The method of claim 5, further comprising generating an output comprising an indication of the updated modelled physical condition and transmitting said output to an electronic device registered to said person or to a medical practitioner caring for said person.

7. The method of claim 5, further comprising adjusting the physiological development model based on the received further input data.

8. The method of claim 5, further comprising, when the predicted change to the physical conditions differs from the further input data by at least the defined threshold:
generating an output of the personalized further digital model of said person for storage on the data storage medium.

9. The method of claim 8, further comprising:
receiving second further input data indicative of a potential further change to the actual physical condition of the organ or system of organs of the person with the communication module;
predicting the second further input data with the personalized digital model and the personalized further digital model respectively based on a period of time elapsed between receiving the further input data and receiving the second further input data using a physiological simulation model; and
selecting one of the personalized digital model and the personalized further digital model as a working digital model based on an accuracy of the predicted second further input data with said models.

10. The method of claim 9, further comprising deleting the personalized digital model or the personalized further digital model if the predicted second further input data generated with said model significantly deviates from the actual second further input data.

11. A computer program product for a personalized digital model of an organ or system of organs of a person for a computer system comprising a processor arrangement and a communication module under control of said processor arrangement, the computer program product comprising a computer readable storage medium having computer readable program instructions embodied therewith for, when executed on the processor arrangement, causing the processor arrangement to implement the following steps:
receive input data relevant to an actual physical condition of the organ or system of organs of the person via the communication module over a first period of time, at least a portion of the input data being received from a wearable sensor device;

search an anatomical model database of digital models modelling different physical conditions of said organ or system of organs and automatically select a digital model from said anatomical model database, wherein the selected digital model comprises an anatomical model for modelling the organ or system of organs and a physiological development model configured to predict changes to a physical condition of the modelled organ or system of organs, wherein the anatomical model of the digital model that is automatically selected most closely matches the actual physical condition of the organ or system of organs of the person based on at least some of the input data;

personalize the selected digital model by developing a modelled physical condition of the selected anatomical model with the physiological development model based on the input data and adjusting the anatomical model such that the modelled physical condition more closely resembles said actual physical condition in accordance with the input data;

predict, using the physiological development model, a change to the physical condition of the modelled organ or system of organs;

receive further input data relevant to the actual physical condition of the organ or system of organs over a second time period later than the first time period;

verify the prediction made by the physiological development model based, at least partially, on a comparison between the predicted change to the physical condition of the modelled organ or system of organs and the further input data; and when the predicted change to the physical condition of the modelled organ or system of organs differs from the further input data by at least a defined threshold:

searching the anatomical model database and automatically selecting a further digital model from the anatomical model database, wherein the selected further digital model comprises an further anatomical model for modelling the organ or system of organs and a further physiological development model configured to predict changes to a physical condition of the modelled organ or system of organs, wherein the further anatomical model of the digital model that is automatically selected most closely matches the actual physical condition of the organ or system of organs of the person based on at least some of the further input data; and personalizing the selected further digital model by developing a further modelled physical condition of the further anatomical model with the further physiological development model based on the further input data and adjusting the further anatomical model such that the further modelled physical condition more closely resembles said actual physical condition in accordance with the further input data;

wherein the further digital model that is automatically selected is different from the digital model that was previously automatically selected.

12. A computer system comprising a processor arrangement and a communication module under control of said processor arrangement, wherein the processor arrangement is adapted to implement the method of claim 1.

13. The computer system of claim 12, further comprising the computer program product communicatively coupled to the processor arrangement.

14. A method of developing a personalized digital model of an organ or system of organs of a person with a computer system comprising a processor arrangement and a communication module under control of the processor arrangement, the method comprising, with said processor arrangement:

receiving input data relevant to an actual physical condition of the organ or system of organs of the person via the communication module over a first period of time, wherein the input data received comprises medical images of the organ or system of organs to be modelled;

searching an anatomical model database of digital models modelling different physical conditions of said organ or system of organs and, using a trained artificial intelligence algorithm, automatically selecting a digital model from said anatomical model database, wherein the selected digital model comprises an anatomical model for modelling the organ or system of organs and a physiological development model configured to predict changes to a physical condition of the modelled organ or system of organs, wherein the anatomical model of the digital model that is automatically selected most closely matches the actual physical condition of the organ or system of organs of the person based on at least some of the input data;

personalizing the selected digital model by developing a modelled physical condition of the selected anatomical model with the physiological development model based on the input data and adjusting the anatomical model such that the modelled physical condition more closely resembles said actual physical condition in accordance with the input data;

predicting, using the physiological development model, a change to the physical condition of the modelled organ or system of organs;

receiving further input data relevant to the actual physical condition of the organ or system of organs over a second time period later than the first time period; and verifying the prediction made by the physiological development model based, at least partially, on a comparison between the predicted change to the physical condition of the modelled organ or system of organs and the further input data;

when the predicted change to the physical condition of the modelled organ or system of organs differs from the further input data by at least a defined threshold:

searching the anatomical model database and automatically selecting a further digital model from the anatomical model database, wherein the selected further digital model comprises an further anatomical model for modelling the organ or system of organs and a further physiological development model configured to predict changes to a physical condition of the modelled organ or system of organs, wherein the further anatomical model of the digital model that is automatically selected most closely matches the actual physical condition of the organ or system of organs of the person based on at least some of the further input data;

personalizing the selected further digital model by developing a further modelled physical condition of the further anatomical model with the further physiological development model based on the further input data and adjusting the further anatomical model such that the further modelled physical condition more closely resembles said actual physical condition in accordance with the further input data;

wherein the further digital model that is automatically selected is different from the digital model that was previously automatically selected.

15. The method of claim 14, wherein the further input data received comprises data from a wearable sensor device associated with the person.

16. The method of claim 11, further comprising:
- predicting an onset, treatment, or development of the actual physical condition of the organ or system of organs of the person over time by developing the modelled physical condition with the physiological development model; and
- generating an output pertaining to said predicted development of the actual physical condition of said person.

17. The method of claim 11, wherein the physiological development model represents a disease model of said organ or system of organs.

18. The method of claim 11, wherein the input data further comprises at least one of information belonging to the person and information belonging to a relative of the person, wherein the at least one of information comprises at least one of a gender, age, weight, imaging data, and lab test data.

19. The computer program product of claim 14, wherein the processor arrangement is further caused to implement the following steps:
- predicting an onset, treatment, or development of the actual physical condition of the organ or system of organs of the person over time by developing the modelled physical condition with the physiological development model; and
- generating an output pertaining to said predicted development of the actual physical condition of said person.

20. The computer program product of claim 14, wherein the physiological development model represents a disease model of said organ or system of organs.

\* \* \* \* \*